United States Patent
Hagadorn et al.

(10) Patent No.: US 9,598,444 B2
(45) Date of Patent: Mar. 21, 2017

(54) TRANSITION METAL COMPLEXES OF TRIDENTATE DIANIONIC CNN LIGANDS, PRODUCTION AND USE THEREOF

(71) Applicant: ExxonMobil Chemical Patents Inc., Baytown, TX (US)

(72) Inventors: John R. Hagadorn, Houston, TX (US); Patrick J. Palafox, Seabrook, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/153,247

(22) Filed: May 12, 2016

(65) Prior Publication Data

US 2017/0002027 A1 Jan. 5, 2017

Related U.S. Application Data

(60) Provisional application No. 62/186,972, filed on Jun. 30, 2015.

(51) Int. Cl.
| | |
|---|---|
| *C08F 4/76* | (2006.01) |
| *C08F 4/64* | (2006.01) |
| *C07F 7/00* | (2006.01) |
| *C08F 110/14* | (2006.01) |
| *C08F 110/02* | (2006.01) |

(52) U.S. Cl.
CPC ............ *C07F 7/00* (2013.01); *C08F 4/64144* (2013.01); *C08F 110/02* (2013.01); *C08F 110/14* (2013.01)

(58) Field of Classification Search
CPC ........... C08F 4/64144; C08F 4/64; C07F 7/00
See application file for complete search history.

(56) References Cited

U.S. PATENT DOCUMENTS

| | | |
|---|---|---|
| 6,103,657 A | 8/2000 | Murray |
| 6,175,409 B1 | 1/2001 | Nielsen et al. |
| 6,260,407 B1 | 7/2001 | Petro et al. |
| 6,294,388 B1 | 9/2001 | Petro |
| 6,294,495 B1 | 9/2001 | Matsunaga |
| 6,306,658 B1 | 10/2001 | Turner et al. |
| 6,406,632 B1 | 6/2002 | Safir et al. |
| 6,436,292 B1 | 8/2002 | Petro |

(Continued)

FOREIGN PATENT DOCUMENTS

| | | |
|---|---|---|
| KR | 10-2011-0031995 | 3/2011 |
| WO | WO00/09255 | 2/2000 |

(Continued)

OTHER PUBLICATIONS

Boussie et al., "Nonconventional Catalysts for Isotactic Propene Polymerization in Solution Developed by Using High-Throughput-Screening Technologies," Polymerization Catalysts, Angew. Chem. Int. Ed., 2006, vol. 45, pp. 3278-3283.

(Continued)

*Primary Examiner* — Rip A Lee (57) ABSTRACT

New pyridylamide transition metal complex compositions for olefin polymerizations are described herein featuring a 7-membered chelate ring and a cyclometalated hydrocarbyl group. When activated using typical activators these compositions form active alkene polymerization catalysts. Theses novel catalyst compositions are shown herein to be active for olefin polymerization, especially for preparation of polymers containing ethylene.

25 Claims, 1 Drawing Sheet

(56) References Cited

U.S. PATENT DOCUMENTS

| | | | |
|---|---|---|---|
| 6,454,947 B1 | 9/2002 | Safir et al. | |
| 6,455,316 B1 | 9/2002 | Turner et al. | |
| 6,461,515 B1 | 10/2002 | Safir et al. | |
| 6,475,391 B2 | 11/2002 | Safir et al. | |
| 6,489,168 B1 | 12/2002 | Wang et al. | |
| 6,491,816 B2 | 12/2002 | Petro | |
| 6,491,823 B1 | 12/2002 | Safir et al. | |
| 6,900,321 B2 | 5/2005 | Boussie et al. | |
| 7,087,690 B2 | 8/2006 | Boussie et al. | |
| 7,858,718 B1 | 12/2010 | Nagy et al. | |
| 7,973,116 B2* | 7/2011 | Hagadorn | C07D 213/38 526/172 |
| 8,158,733 B2 | 4/2012 | Nagy et al. | |
| 8,592,615 B2* | 11/2013 | Kuhlman | C07D 521/00 502/113 |
| 9,315,526 B2* | 4/2016 | Hagadorn | C07F 7/00 |
| 9,315,593 B2* | 4/2016 | Hagadorn | C08F 4/65912 |
| 2002/0142912 A1* | 10/2002 | Boussie | C08F 10/00 502/152 |
| 2004/0220050 A1 | 11/2004 | Frazier et al. | |
| 2005/0222443 A1* | 10/2005 | Vogel | C07F 7/28 556/51 |
| 2011/0224391 A1 | 9/2011 | Hagadorn et al. | |

FOREIGN PATENT DOCUMENTS

| | | |
|---|---|---|
| WO | WO02/46249 | 6/2002 |
| WO | WO2005/095469 | 10/2005 |
| WO | WO2007/067965 | 6/2007 |
| WO | WO2010/037059 | 4/2010 |

OTHER PUBLICATIONS

Boussie et al., "A Fully Integrated High-Throughput Screening Methodology for the Discovery of New Polyolefin Catalysts: Discovery of a New Class of High Temperature Single-Site Group (IV) Copolymerization Catalysts," Journal of American Chemical. Society, 2003, vol. 125, pp. 4306-4317.

Britovsek, G.J.P. et al., "The Search for New-Generation Olefin Polymerization Catalysts: Life beyond Metallocenes," Angew. Chem. Int. Ed., 1999, vol. 38, pp. 428-447.

Domski, G.J. et al., "Living alkene polymerization: New methods for the precision synthesis of polyolefins," ScienceDirect, Prog. Polym. Sci., 2007, vol. 32, pp. 30-92.

Froese, R.D.J. et al., Mechanism of Activation of a Hafnium Pyridyl-Amide Olefin Polymerization Catalyst: Ligand modification by Monomer, Jrnl. Am. Chem. Soc., 2007, vol. 129, pp. 7831-7840.

Giambastiani, G. et al., "Imino- and Amido-Pyridinate d-Block Metal Complexes in Polymerization/Oligomerization Catalysis," Ch. 5 in Olefin Upgrading Catalysis by Nitrogen-based Metal Complexes I, Catalysis by Metal Complexes, Springer, 2011, pp. 197-281.

Gibson, V.C. et al., "Advances in Non-Metallocene Olefin Polymerization Catalysis," Chem. Rev., 2003, vol. 103, p. 283-315.

Vaughan, A. et al., "Industrial catalysts for alkene polymerization," Comprehensive Polymer Science, 2012, vol. 3, Ch. 20, pp. 657-671.

* cited by examiner

TRANSITION METAL COMPLEXES OF TRIDENTATE DIANIONIC CNN LIGANDS, PRODUCTION AND USE THEREOF

CROSS REFERENCE TO RELATED APPLICATIONS

This invention claims priority to and the benefit of U.S. Ser. No. 62/186,972, filed Jun. 30, 2015.

FIELD OF THE INVENTION

The invention relates to transition metal complexes of tridentate dianionic CNN ligands and intermediates and processes for use in making such complexes. The tridentate ligands in these complexes chelate to the metal center with the formation of one 5-membered and one 7-membered ring, for the rings formed by coordination of the carbanion and amido donors, respectively. The transition metal complexes may be used as catalysts for alkene polymerization processes.

BACKGROUND OF THE INVENTION

Pyridyl amines have been used to prepare Group 4 complexes, which are useful transition metal components in the polymerization of alkenes, see for example, US 2002/0142912, U.S. Pat. No. 6,900,321, and U.S. Pat. No. 6,103,657, where the ligands have been used in complexes in which the ligands are coordinated in a bidentate fashion to the transition metal atom.

WO 2005/095469 shows catalyst compounds that use tridentate ligands through two nitrogen atoms (one amido and one pyridyl) and one oxygen atom.

US 2004/0220050A1 and WO 2007/067965 disclose group 4 transition metal pyridylamide complexes in which the ligand is coordinated in a tridentate fashion through two nitrogen (one amido and one pyridyl) and one carbon (aryl anion) donor. The amido donor in these complexes does not coordinate to the transition metal with the formation of a 7-membered ring.

A key step in the activation of these complexes is the insertion of an alkene into the metal-aryl bond of the catalyst precursor (Froese, R. D. J. et al., J. Am. Chem. Soc., 2007, Vol. 129, pp. 7831-7840) to form an active catalyst. The coordination of the amido donor group in these complexes forms a 5-membered ring instead of a 7-membered ring.

U.S. Pat. No. 7,973,116 B2 discloses group 4 pyridyldiamide complexes that are useful as catalyst components for olefin polymerization processes. These complexes feature tridentate dianionic ligands that coordinate to the metal center through three nitrogen donor groups.

Other references of interest include: 1) Domski, G. J.; Rose, J. M.; Coates, G. W.; Bolig, A. D.; Brookhart, M., "Living alkene polymerization: New methods for the precision synthesis of polyolefins," Prog. Polym. Sci., 2007, Vol 32, pp. 30-92; 2) Giambastiani, G.; Laconi, L.; Kuhlman, R. L.; Hustad, P. D., "Imino- and amido-pyridinate d-block metal complexes in polymerization/oligomerization catalysis," Chapter 5 in Olefin Upgrading Catalysis by Nitrogen-based Metal Complexes I, Catalysis by Metal Complexes, Springer, 2011; 3) Vaughan, A; Davis, D. S.; Hagadom, J. R., "Industrial catalysts for alkene polymerization", Comprehensive Polymer Science, 2012, Vol. 3, Chapter 20; 4) Gibson, V. C.; Spitzmesser, S. K. Chem. Rev., 2003, Vol. 103, p. 283; 5) Britovsek, G. J. P.; Gibson, V. C.; Wass, D. F.; Angew. Chem. Int. Ed., 1999, Vol. 38, p. 428; 6) WO 2010/037059; 7) Boussie, Thomas R. et al. "Non-conventional Catalysts for Isotactic Propene Polymerization in Solution Developed by Using High-Throughput-Screening Technologies" Angew. Chem. Int. Ed. 2006, 45, 3278-3283; 8) U.S. Pat. No. 8,674,040; and 9) U.S. Pat. No. 7,087,690.

There still is need for new catalysts complexes with enhanced performance in alkene polymerization.

Further, there is a need in the art for new catalysts that are capable of producing high molecular weight polymers at high process temperatures, including highly crystalline polypropylene and ethylene copolymers with alpha olefins.

SUMMARY OF THE INVENTION

New catalyst compositions for olefin polymerizations are described herein featuring a tridentate dianionic ligand that coordinates to the metal with one carbanion group, one neutral nitrogen donor group, and one anionic amido group. This tridentate "CNN" ligand, which has a central neutral donor, is chelated to the metal so that the amido donor group forms a 7-membered ring and the carbanion group forms a 5-membered ring. The presence of the 7-membered ring is important because it makes the complex chiral (C1 symmetric) on the timescale relevant for polymer chain growth, which is a desirable feature for catalysts making isotactic poly(alpha-olefins), such as isotactic polypropylene. When activated using typical activators, these compositions form active alkene polymerization catalysts. Theses novel catalyst compositions are shown herein to be active for olefin polymerization, especially for preparation of polymers containing ethylene.

This invention relates to novel transition metal complexes having tridentate dianionic CNN ligands. This invention also relates to heterocyclic amido, pyridylamido, and related transition metal complexes represented by the Formula (I):

wherein:

M is a Group 3, 4 or 5 metal;

Q is -(TT)- or -(TTT)-, where each T is a substituted or unsubstituted group 14, 15, or 16 element so that together with the "—C—N=C—" fragment it forms a 5- or 6-membered heterocycle;

$R^1$ is selected from hydrocarbyls, substituted hydrocarbyls (such as halocarbyls, substituted halocarbyls, silylcarbyls), and polar groups;

each $R^2$ and $R^3$ is independently selected from hydrogen, halogen, hydrocarbyls, substituted hydrocarbyls (such as halocarbyls, substituted halocarbyls, silylcarbyls), and polar groups, and $R^2$ and $R^3$ may be joined to form a ring;

each $R^4$, $R^5$, $R^6$, and $R^7$ is independently selected from hydrogen, halogen, hydrocarbyls, substituted hydrocarbyls (such as halocarbyls, substituted halocarbyls, silylcarbyls), and polar groups, and any adjacent R groups may join to form carbocyclic or heterocyclic ring, which may be substituted or unsubstituted;

$R^3$ and $R^4$ may be joined to form a ring;

J is an aromatic group containing 4 to 40 carbon atoms that coordinates to the metal center through a carbanion donor;

each X is an anionic leaving group, where the X groups may be the same or different and any two X groups may be linked to form a dianionic leaving group;

each L is a neutral Lewis base and any two L groups may be joined to form a bidentate Lewis base;

X and L groups may be covalently joined;

n is 1, 2, or 3;

y is 0, 1, or 2;

wherein n+y is no greater than 4.

This invention further relates to process to make the above complex, process to make intermediates for the above complex, and methods to polymerize olefins using the above complex.

DETAILED DESCRIPTION OF THE INVENTION

Figure 1:
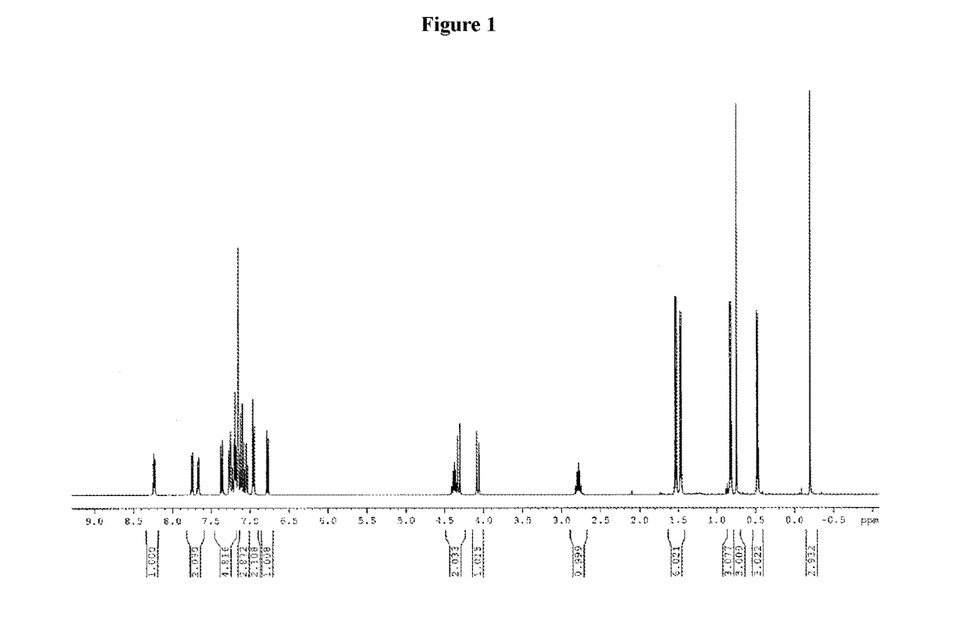
FIG. 1 is a 400 MHz 1H-NMR spectrum of complex B acquired as a ~0.02 M solution in C6D6 and referenced to residual C6D5H at δ 7.15 ppm.
Figure 2:
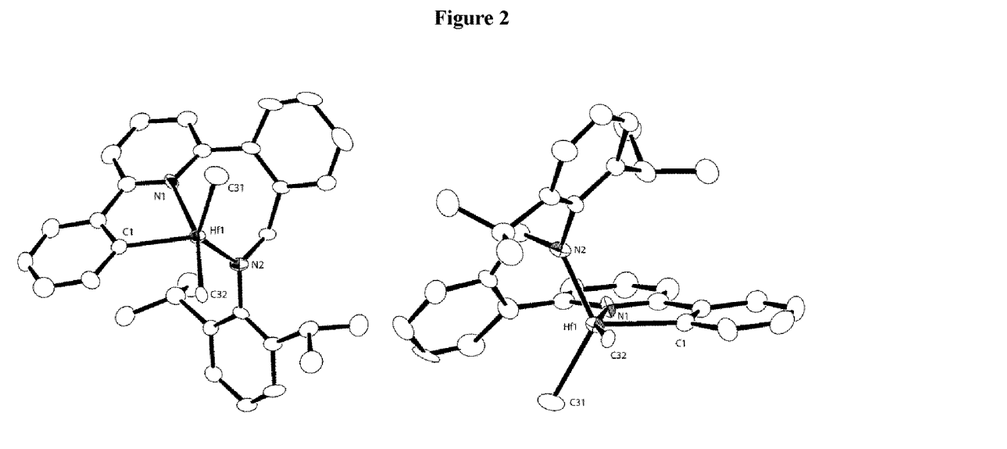
FIG. 2 displays two views of the molecular structure of complex B as determined by single-crystal X-ray diffraction drawn as 30% thermal ellipsoids.

The specification describes transition metal complexes. The term complex is used to describe molecules in which an ancillary ligand is coordinated to a central transition metal atom. The ligand may be coordinated to the transition metal by covalent bond and/or electron donation coordination or intermediate bonds. The transition metal complexes are generally subjected to activation to perform their polymerization or oligomerization function using an activator, which is believed to create a cation as a result of the removal of an anionic group, often referred to as a leaving group, from the transition metal.

As used herein, the numbering scheme for the Periodic Table groups is the new notation as set out in Chemical and Engineering News, 1985, Vol. 63(5), p. 27.

As used herein, Me is methyl, Et is ethyl, Bu is butyl, t-Bu is tertiary butyl, Pr is propyl, iPr is isopropyl, THF (also referred to as thf) is tetrahydrofuran, Bn is benzyl, Ph is phenyl, RT is room temperature.

The terms "hydrocarbyl radical," "hydrocarbyl," and "hydrocarbyl group" are used interchangeably throughout this document. Likewise, the terms "group," "radical," and "substituent" are also used interchangeably in this document. For purposes of this disclosure, "hydrocarbyl radical" is defined to be a C1-C100 radical, that may be linear, branched, or cyclic, and when cyclic, aromatic or non-aromatic.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g., F, Cl, Br, I) or halogen-containing group (e.g., $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure. Preferred silylcarbyls are of formula $SiR^*_3$.

Polar radicals or polar groups are groups in which the heteroatom functionality is bonded directly to the indicated atom or atoms. They include heteroatoms of groups 13-17 of the periodic table either alone or connected to other elements by covalent or other interactions such as ionic, van der Waals forces, or hydrogen bonding. Examples of polar groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, and aluminates. Polar groups also include organic polymer supports or inorganic support material such as alumina, and silica. Preferred examples of polar groups include $NR^*_2$, $OR^*$, $SeR^*$, $TeR^*$, $PR^*_2$, $AsR^*_2$, $SbR^*_2$, $SR^*$, $BR^*_2$, $SnR^*_3$, $PbR^*_3$ and the like where R* is independently a hydrocarbyl, substituted hydrocarbyl, halocarbyl or substituted halocarbyl radical as defined above and two R* may join together to form a substituted or unsubstituted saturated, partially unsaturated or aromatic cyclic or polycyclic ring structure. Most preferred examples of polar groups include $NR^*_2$ and $PR^*_2$.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

Complex, as used herein, is also often referred to as catalyst precursor, precatalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. Some scavengers may also act as chain-transfer agents. A co-activator, that is not a scavenger, may also be used in conjunction with an activator in order to form an active catalyst. In some embodiments, a co-activator can be pre-mixed with the transition metal compound to form an alkylated transition metal compound.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

For the purposes of this invention, ethylene shall be considered an α-olefin.

As used herein, Mn is number average molecular weight, Mw is weight average molecular weight, and Mz is z average molecular weight, wt % is weight percent, and mol % is mole percent. Molecular weight distribution (MWD), also referred to as polydispersity, is defined to be Mw divided by Mn. Unless otherwise noted, all molecular weight units (e.g., Mw, Mn, Mz) are g/mol.

Unless otherwise noted all melting points (Tm) are DSC second melt.

A "ring carbon atom" is a carbon atom that is part of a cyclic ring structure. By this definition, a benzyl group has 6-ring carbon atoms and para-methylstyrene also has 6-ring carbon atoms.

The term "aryl" or "aryl group" means a six carbon aromatic ring and the substituted variants thereof, including but not limited to, phenyl, 2-methyl-phenyl, xylyl, 4-bromoxylyl. Likewise heteroaryl means an aryl group where a ring carbon atom (or 2- or 3-ring carbon atoms) has been replaced with a heteroatom, preferably N, O, or S.

The term "ring atom" means an atom that is part of a cyclic ring structure. By this definition, a benzyl group has 6-ring atoms and tetrahydrofuran has 5 ring atoms.

The terms "heterocycle" and "heterocyclic ring" are used interchangeably.

A heterocyclic ring is a ring having a heteroatom in the ring structure as opposed to a heteroatom substituted ring where a hydrogen on a ring atom is replaced with a heteroatom. For example, tetrahydrofuran and pyridine are heterocyclic rings and N,N-dimethylaminobenzene is not a heterocycle, but instead is a substituted aryl group.

As used herein the term "aromatic" refers to 6-membered carbocycles with alternating single and double bonds, such as benzene and related derivatives. Additionally the term as used herein also refers to heterocycles and substituted heterocycles that have properties and structures (nearly planar) that are similar to aromatics. Examples of such molecules include pyridines, carbazoles, imidazoles, oxazoles, and thiazoles.

The term "continuous" means a system that operates without interruption or cessation. For example, a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng, Chem. Res., 2000, Vol. 29, p. 4627.

A bulk polymerization means a polymerization process in which the monomers and/or comonomers being polymerized are used as a solvent or diluent using little or no inert solvent as a solvent or diluent. A small faction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

Unless otherwise stated, "catalyst activity" is a measure of how many grams of polymer (P) are produced using a polymerization catalyst comprising W mmol of transition metal, over a period of time of T hours; and may be expressed by the following formula: $P/(T \times W)$.

This invention provides new catalyst compounds of group 4 pyridylamides that feature both: (1) a 7-membered chelate ring containing an amido donor group and the pyridine donor group, and (2) a 5-membered chelate ring containing a metalated carbanionic donor group and the pyridine donor group. These catalysts are useful for the production of a broad range of polyolefins including polyethylene, ethylene-alpha-olefin copolymer, isotactic polypropylene (iPP), polyalphaolefin (PAO), ethylene propylene copolymer rubber (EPR), and ethylene propylene diene monomer copolymer (EPDM).

This invention also relates to process to polymerize olefins comprising contacting olefins with a catalyst system comprising an activator and one or more compounds represented by the Formula (I), (II), or (III):

(I)

(II)

(III)

wherein:
M is a Group 3, 4 or 5 metal;
Q is -(TT)- or -(TTT)-, where each T is a substituted or unsubstituted group 14, 15, or 16 element so that together with the "—C—N=C—" fragment it forms a 5- or 6-membered heterocycle;
$R^1$ is selected from hydrocarbyls, substituted hydrocarbyls (such as halocarbyls, substituted halocarbyls, silylcarbyls), and polar groups;
each $R^2$ and $R^3$ is independently selected from hydrogen, halogen, hydrocarbyls, substituted hydrocarbyls (such as halocarbyls, substituted halocarbyls, silylcarbyls), and polar groups, and $R^2$ and $R^3$ may be joined to form a ring;
each $R^4$, $R^5$, $R^6$, $R^7$, $R^8$, $R^9$, $R^{10}$, $R^{11}$, $R^{12}$, $R^{13}$, and $R^{14}$, is independently selected from hydrogen, halogen, hydrocarbyls, substituted hydrocarbyls (such as halocarbyls, substituted halocarbyls, silylcarbyls), and polar groups, and any adjacent R groups may join to form carbocyclic or heterocyclic ring, which may be substituted or unsubstituted;
$R^3$ and $R^4$ may be joined to form a ring and $R^{10}$ and $R^{11}$ may be joined to form a ring (preferably a 5-membered ring with the joined $R^3R^4$ group being —CH$_2$CH$_2$—, or a six-membered ring with the joined $R^{10}R^{11}$ group being —CH$_2$CH$_2$CH$_2$—);
J is an aromatic group containing 4 to 40 carbon atoms that coordinates to the metal center through a carbanion donor;
each X is an anionic leaving group, where the X groups may be the same or different and any two X groups may be linked to form a dianionic leaving group;
each L is a neutral Lewis base and any two L groups may be joined to form a bidentate Lewis base;
X and L groups may be covalently joined;
n is 1, 2, or 3;
y is 0, 1, or 2;
wherein n+y is no greater than 4.

In a preferred embodiment, the olefins comprise ethylene and/or propylene.

Catalyst Complexes

In a first aspect of the invention there is provided a transition metal complex (optionally for use in alkene polymerization) represented by the Formula (I), (II), or (III):

(I)

(II)

(III)

wherein:
M is a Group 3, 4 or 5 metal, preferably Hf, Zr, Ti, Sc, Y, V, Na or Ta, preferably Hf, Zr or Ti;
Q is -(TT)- or -(TTT)-, where each T is a substituted or unsubstituted group 14, 15, or 16 element so that together with the "—C—N=C—" fragment it forms a 5- or 6-membered heterocycle;
$R^1$ is selected from hydrocarbyls, substituted hydrocarbyls (such as halocarbyls, substituted halocarbyls, silylcarbyls), and polar groups;
each $R^2$ and $R^3$ is independently selected from hydrogen, halogen, hydrocarbyls, substituted hydrocarbyls (such as halocarbyls, substituted halocarbyls, silylcarbyls), and polar groups, and $R^2$ and $R^3$ may be joined to form a ring;
each $R^4$, $R^5$, $R^6$, $R^7$, $R^8$, $R^9$, $R^{10}$, $R^{11}$, $R^{12}$, $R^{13}$, and $R^{14}$ is independently selected from hydrogen, halogen, hydrocarbyls, substituted hydrocarbyls (such as halocarbyls, substituted halocarbyls, silylcarbyls) and polar groups, and any adjacent R groups may join to form a carbocyclic or heterocyclic ring, which may be substituted or unsubstituted;

$R^3$ and $R^4$ may be joined to form a ring and $R^{10}$ and $R^{11}$ may be joined to form a ring (preferably a 5-membered ring with the joined $R^3R^4$ group being —$CH_2CH_2$—, or a 6-membered ring with the joined $R^{10}R^{11}$ group being —$CH_2CH_2CH_2$—);

J is an aromatic group containing 4 to 40 carbon atoms that coordinates to the metal center through a carbanion donor;

X is an anionic leaving group, where the X groups may be the same or different and any two X groups may be linked to form a dianionic leaving group;

L is a neutral Lewis base and any two L groups may be joined to form a bidentate Lewis base;

X and L groups may be covalently joined;

n is 1, 2, or 3;

y is 0, 1, or 2;

wherein n+y is no greater than 4.

In Formula (I), (II), and (III) above, the dashed lines represent optional bonds and solid lines represent bonds. The J group is an aromatic group containing at least 6 carbons that is bound to the metal center in a manner that forms a 5-membered, or 6-membered, or 7-membered chelate ring. The Q group is a carbon-containing fragment that joins with the CNC fragment to form an aromatic heterocyclic ring, such as a pyridine, imidazole, thioimidazole, and the like.

In any embodiment of the invention described herein, M may be a group 3, 4, or 5 transition metal, preferably Ti, Zr, or Hf, most preferably Zr or Hf.

In any embodiment of the invention described herein, $R^1$ is a selected from the group consisting of: hydrocarbyls (such as alkyls and aryls), substituted hydrocarbyls (such as heteroaryls), and silyl groups, preferably $R^1$ is a selected from methyl, ethyl, propyl, butyl, pentyl, hexyl, heptyl, octyl, nonyl, decyl, phenyl, and isomers thereof.

In any embodiment of the invention described herein, $R^1$ may be selected from the group consisting of hydrocarbyls, substituted hydrocarbyls, halocarbyls, substituted halocarbyls, silylcarbyls, and polar groups, preferably $R^1$ is selected from phenyl groups that are variously substituted with between zero to five substituents that include F, Cl, Br, I, $CF_3$, NO2, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof. Some specific examples would include R1 being chosen from a group including 2-methylphenyl, 2-isopropylphenyl, 2-ethylphenyl, 2,6-dimethylphenyl, mesityl, 2,6-diethylphenyl, 2,6-diisopropylphenyl, and 2,4,6-triisopropylphenyl.

In any embodiment of the invention described herein, each $R^2$ and $R^3$ is independently selected from the group consisting of hydrogen, halogen, hydrocarbyls, substituted hydrocarbyls (such as halocarbyls, substituted halocarbyls, silylcarbyls), and polar groups, and $R^2$ and $R^3$ may be joined to form a ring.

In any embodiment of the invention described herein, each $R^4$, $R^5$, $R^6$, $R^7$, $R^8$, $R^9$, $R^{10}$, $R^{11}$, $R^{12}$, $R^{13}$, and $R^{14}$ is independently selected from hydrogen, halogen, hydrocarbyls, substituted hydrocarbyls (such as halocarbyls, substituted halocarbyls, silylcarbyls), and polar groups, and any adjacent R groups may join to form carbocyclic or heterocyclic ring, which may be substituted or unsubstituted. Preferred groups for $R^4$, $R^5$, $R^6$, $R^7$, $R^8$, $R^9$, $R^{10}$, $R^{11}$, $R^{12}$, $R^{13}$, and $R^{14}$, include hydrogen, floro, chloro, methyl, ethyl, propyl, butyl, pentyl, hexyl, heptyl, octyl, nonyl, decyl, and isomers thereof.

In any embodiment of the invention described herein, Q is -(TT)- or -(TTT)-, where each T is a substituted or unsubstituted hydrocarbyl group 14, 15, or 16 element so that together with the "—C—N═C—" fragment it forms a 5- or 6-membered heterocycle, preferred Q groups include —C(H)C(H)C(H)—, —C(H)N(Me)-, —C(H)N(Et)-, —C(H)O—, and —C(H)S—.

In any embodiment of the invention described herein, J may be an aromatic group containing 4 to 40 carbon atoms that coordinates to the metal center through a carbanion donor, preferred J groups include $C_6H_4$, $C_{10}H_6$, $C_{12}H_7N$, and $C_{14}H_8$.

In any embodiment of the invention described herein, preferably X is selected from halide, alkyl, aryl, alkoxy, amido, hydrido, phenoxy, hydroxy, alkylsulfonate, carboxylate, silyl, allyl, alkenyl, and alkynyl, preferably methyl, chloro, trifluoromethanesulfonate, dimethylamido, and diethylamido. The selection of the leaving groups depends on the synthesis route adopted for arriving at the complex and may be changed by additional reactions to suit the later activation method in polymerization. For example, a preferred X is alkyl when using non-coordinating anions such as N,N-dimethylanilinium tetrakis(pentafluorophenyl)-borate or tris(pentafluorophenyl)borane. In another embodiment, two X groups may be linked to form a dianionic leaving group, for example, oxalate.

In any embodiment of the invention described herein, preferably L is selected from ethers, thio-ethers, amines, nitriles, imines, pyridines, and phosphines, preferably ethers, preferably $Et_2O$, dimethylamine, diethylamine, tetrahydrofuran, and tetrahydrothiophene.

In any embodiment of the invention described herein, n is 1, 2, or 3 and y is 0, 1, or 2, where n+y is no greater than 4, preferably n is 1 or 2 and y is 0 or 1, and n+y is 2. Alternately n is 2, y is 0 and n+y is 2.

In any embodiment of the invention described herein, M is Sc, Y, Ti, Zr, Hf, V, Nb, or Ta; and $R^2$ and $R^3$ may be, independently, hydrogen, a $C_1$ to $C_{20}$ alkyl, preferably methyl, ethyl, propyl, butyl, pentyl, hexyl, heptyl, octyl, nonyl, decyl, undecyl, dodecyl, or an isomer thereof), or a $C_5$ to $C_{40}$ aryl group (preferably a $C_6$ to $C_{20}$ aryl group, preferably phenyl or substituted phenyl or an isomer thereof, preferably phenyl, 2-isopropylphenyl, or 2-tertbutylphenyl).

In any embodiment of the invention described herein, $R^1$ contains from 1 to 30 carbon atoms, preferably from 2 to 20 carbon atoms.

In any embodiment of the invention described herein, M may be Ti, Zr, or Hf, and $R^1$ is 2,6-dialkylphenyl with Zr or Hf based complexes being especially preferred.

In any embodiment of the invention described herein, M is Zr or Hf, $R^2$ and $R^3$ are both hydrogen, and J is an aromatic carbocycle containing between 6 and 14 carbons.

In any embodiment of the invention described herein, M is a group 4 metal, $R^2$ is hydrogen, $R^3$ and $R^4$ are joined to form a 5-membered ring, with the $R^3R^4$ unit being —$CH_2CH_2$—.

In any embodiment of the invention described herein, M is a group 4 metal, $R^2$ is hydrogen, $R^3$ and $R^4$ are joined to form a 6-membered ring, with the $R^3R^4$ unit being —$CH_2CH_2CH_2$—.

In any embodiment of the invention described herein, M is a group 4 metal, $R^2$ is hydrogen, $R^{10}$ and $R^{11}$ are joined to form a 6-membered ring, with the $R^{10}R^{11}$ unit being —$CH_2CH_2CH_2$—.

In a preferred embodiment, the transition metal complex is represented by the Formula (III) above, y is 0, and M is a Group 4 metal preferably Zr or Hf, preferably Hf.

In a preferred embodiment, $R^2$ is H and $R^3$ is a group containing between 1 to 100 (preferably 6 to 40, preferably

6 to 30) carbons, M is a Group 4 metal (preferably Zr or Hf, preferably Hf), alternately $R^2$ is the same as $R^3$ and is preferably hydrogen or methyl.

In another aspect of the invention, there are provided various processes for synthesizing the complexes described herein.

Ligand Synthesis

The CNN ligands, which are used to prepare the complexes described herein, can be prepared according to the general scheme presented below. Pyridine substituted with aromatic groups (Int-1) are well known in the literature and some are available from commercial sources (e.g., 2-phenylpyridine from Sigma-Aldrich). Int-1 may be deprotonated in the ortho-position using a strong base, such 2:1 butyllithium:N,N-dimethylaminoethanol (for examples, see: Journal of Organic Chemistry, 2003, Vol. 68, p. 2028). This lithiated species may be reacted with an electophilic Br source, such as tetrabromomethane or 1,2-dibromoethane to afford Int-2. Int-2 may be coupled with boronic acid ester Int-3 using a Pd catalyst, such as $Pd(PPh_3)_4$. Boronic acid esters of the formula shown as Int-3 may be prepared as described in US 2014/0221587, US 2014/0316089, and US 2015/0141601. The CNN ligands prepared by this method may be purified by crystallization, chromatography, or by isolation of their salts formed by reaction of the neutral CNN ligand with an acid, followed by washing and deprotonation by reaction with a base.

and amidos. Some transition metal reagents of use for these transformations are $ZrBn_4$, $HfBn_4$, $TiBn_4$, $Zr(NMe_2)_4$, $Hf(NMe_2)_4$, $Hf(NMe_2)_2C1_2$(1,2-dimethoxyethane), $ZrBn_2C1_2(OEt_2)$, $HfBnC1_2(OEt_2)x$, $TaMe_3C1_2$, and $TaMe_2C1_3$. In the transition metal reagents that contain mixed X groups, the less reactive anionic X groups, typically chloride, will remain on the transition metal and the more reactive X groups will be eliminated as their corresponding conjugate acid, XH.

CNN ligand where $R^1$, $R^2$, $R^3$, $R^4$, $R^5$, $R^6$, $R^7$, $R^8$, $R^9$, $R^{10}$ are as described above, and HJ is an non-coordinated aromatic group containing 4 to 40 carbon atoms that can be deprotonated to form a group that coordinates to the metal center through a carbanion donor.

The CNN ligands may be complexed to group 3-5 transition metals using a variety of known methods. One generally useful method is shown below. This involves the direct reaction of the neutral CNN ligand with a basic organometallic reagent $M(X)n+2$, where X is an anionic leaving group that is capable of reacting with two protons of the neutral CNN ligand to form the resulting transition metal complex with the elimination of two equivalents of XH. Common reactive X groups include hydrides, hydrocarbyls,

-continued

CNN complex where M, X, n, L, y, $R^1$, $R^2$, $R^3$, $R^4$, $R^5$, $R^6$, $R^7$, $R^8$, $R^9$, $R^{10}$, $R^{11}$, $R_{12}$, $R^{13}$, and $R^{14}$ are as described above.

Reaction of the CNN ligand with M(X)n+2 may initially result in the formation of an intermediate complex, with a bidentate coordinated ligand that is bound to the M(X)n+1 fragment through the amido nitrogen and the neutral Lewis base. An example of this bidentate species is shown below as the "intermediate bidentate complex". This intermediate species may be isolated and even used as a catalyst component with typical activators because it is converted to the inventive CNN complex, featuring a tridentate CNN ligand, upon further reaction. The bidentate intermediate may be formed by reaction of the CNN ligand a transition metal amide reagent, such as M(amido)4, where M is a group 4 metal, under relatively mild conditions (i.e., lower temperatures). The bidentate intermediate may be converted to the CNN complex (I) by heating or other methods that cause it to eliminate HX, with the hydrogen being derived from the J group.

intermediate bidentate complex (I)

where HJ, J, Q, M, X, n, L, y, $R^1$, $R^2$, $R^3$, $R^4$, $R^5$, $R^6$, and $R^7$ are as described above.

An alternative route to CNN complexes involves the reaction of the neutral CNN ligand with a group 1 or 2 base to form an amido salt, such as Li[CNN ligand]. This anionic CNN species could then be reacted with a transition metal halide M(halide)n+2 to form a bidentate complex of the general formula [bidentate CNN ligand]M(halide)n+1. Reaction of this species with an alkylating reagent, such as MeMgBr or MeLi, would be expected to form the tridentate CNN complex [CNN]M(alkyl)n, with the elimination of lithium halide and alkyl-H. An example of this alternative route would be to react the CNN ligand with one equivalent of butyllithium to generate the lithium amido species. This lithium salt could then be reacted with $HfCl_4$ to form a species of the Formula [bidentate CNN ligand]$HfCl_3$, with the loss of LiCl. Methylation of this species with MeLi would initially form [bidentate CNN ligand]$HfMe_3$, which would be expected to eliminate methane to form the tridentate complex [CNN]$HfMe_2$.

Activators

After the complexes have been synthesized, catalyst systems may be formed by combining them with activators in any manner known from the literature, including by supporting them for use in slurry or gas phase polymerization.

The catalyst systems may also be added to or generated in solution polymerization or bulk polymerization (in the monomer). The catalyst system typically comprises a complex as described above and an activator such as alumoxane or a non-coordinating anion. Activation may be performed using alumoxane solution including methyl alumoxane, referred to as MAO, as well as modified MAO, referred to herein as MMAO, containing some higher alkyl groups to improve the solubility. Particularly, useful MAO can be purchased from Albemarle, typically in a 10 wt % solution in toluene. The catalyst system employed in the present invention preferably uses an activator selected from alumoxanes, such as methyl alumoxane, modified methyl alumoxane, ethyl alumoxane, iso-butyl alumoxane, and the like.

When an alumoxane or modified alumoxane is used, the complex-to-activator molar ratio is from about 1:3000 to 10:1; alternatively 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-complex ratio is 1:1 molar ratio.

Activation may also be performed using non-coordinating anions, referred to as NCA's, of the type described in EP 277 003 and EP 277 004. NCA may be added in the form of an ion pair using, for example, [DMAH]+[NCA]− in which the N,N-dimethylanilinium (DMAH) cation reacts with a basic leaving group on the transition metal complex to form a transition metal complex cation and [NCA]-. The cation in the precursor may, alternatively, be trityl. Alternatively, the transition metal complex may be reacted with a neutral NCA precursor, such as $B(C_6F_5)_3$, which abstracts an anionic group from the complex to form an activated species. Useful activators include N,N-dimethylanilinium tetrakis (pentafluorophenyl)borate (i.e., [$PhNMe_2H$]$B(C_6F_5)_4$) and N,N-dimethylanilinium tetrakis (heptafluoronaphthyl)borate, where Ph is phenyl, and Me is methyl.

Additionally preferred activators useful herein include those described in U.S. Pat. No. 7,247,687 at column 169, line 50 to column 174, line 43, particularly column 172, line 24 to column 173, line 53.

Noncoordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

In an embodiment of the invention described herein, the non-coordinating anion activator is represented by the following Formula (1):

$$(Z)_d^+(A^{d-}) \quad (1)$$

wherein Z is (L-H) or a reducible Lewis acid; L is a neutral Lewis base; H is hydrogen and (L-H)$^+$ is a Bronsted acid; A$^{d-}$ is a non-coordinating anion having the charge d−; and d is an integer from 1 to 3.

When Z is (L-H) such that the cation component is (L-H)d+, the cation component may include Bronsted acids such as protonated Lewis bases capable of protonating a moiety, such as an alkyl or aryl, from the catalyst precursor, resulting in a cationic transition metal species, or the activating cation (L-H)d$^+$ is a Bronsted acid, capable of donating a proton to the catalyst precursor resulting in a transition metal cation, including ammoniums, oxoniums, phosphoniums, silyliums, and mixtures thereof, or ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid, it may be represented by the Formula: (Ar$_3$C$^+$), where Ar is aryl or aryl substituted with a heteroatom, or a C1 to C40 hydrocarbyl, the reducible Lewis acid may be represented by the Formula: (Ph$_3$C$^+$), where Ph is phenyl or phenyl substituted with a heteroatom, and/or a C1 to C40 hydrocarbyl. In an embodiment, the reducible Lewis acid is triphenyl carbenium.

Embodiments of the anion component Ad− include those having the Formula [Mk+Qn]d− wherein k is 1, 2, or 3; n is 1, 2, 3, 4, 5, or 6, or 3, 4, 5, or 6; n−k=d; M is an element selected from Group 13 of the Periodic Table of the Elements, or boron or aluminum, and Q is independently a hydride, bridged or unbridged dialkylamido, halide, alkoxide, aryloxide, hydrocarbyl radicals, said Q having up to 20 carbon atoms with the proviso that in not more than one occurrence is Q a halide, and two Q groups may form a ring structure. Each Q may be a fluorinated hydrocarbyl radical having 1 to 20 carbon atoms, or each Q is a fluorinated aryl radical, or each Q is a pentafluoryl aryl radical. Examples of suitable Ad− components also include diboron compounds as disclosed in U.S. Pat. No. 5,447,895, which is fully incorporated herein by reference.

In an embodiment in any of the NCA's represented by Formula 1 described above, the anion component Ad− is represented by the Formula [M*k*+Q*n*]d*− wherein k* is 1, 2, or 3; n* is 1, 2, 3, 4, 5, or 6 (or 1, 2, 3, or 4); n*−k*=d*; M* is boron; and Q* is independently selected from hydride, bridged or unbridged dialkylamido, halogen, alkoxide, aryloxide, hydrocarbyl radicals, said Q* having up to 20 carbon atoms with the proviso that in not more than 1 occurrence is Q* a halogen.

This invention also relates to a method to polymerize olefins comprising contacting olefins (such as propylene) with a catalyst complex as described above and an NCA activator represented by the Formula (2):

$$R_nM^{**}(ArNHal)_{4-n} \quad (2)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula 2 also comprises a suitable cation that is essentially non-interfering with the ionic catalyst complexes formed with the transition metal compounds, or the cation is Z$_d^+$ as described above.

In an embodiment in any of the NCA's comprising an anion represented by Formula 2 described above, R is selected from the group consisting of C1 to C30 hydrocarbyl radicals. In an embodiment, C1 to C30 hydrocarbyl radicals may be substituted with one or more C1 to C20 hydrocarbyl radicals, halide, hydrocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means C4 to C20 hydrocarbyl radicals; —SR$^a$, —NR$^a_2$, and —PR$^a_2$, where each R$^a$ is independently a monovalent C4 to C20 hydrocarbyl radical comprising a molecular volume greater than or equal to the molecular volume of an isopropyl substitution or a C4 to C20 hydrocarbyl substituted organometalloid having a molecular volume greater than or equal to the molecular volume of an isopropyl substitution.

In an embodiment in any of the NCA's comprising an anion represented by Formula 2 described above, the NCA also comprises cation comprising a reducible Lewis acid represented by the Formula: (Ar$_3$C+), where Ar is aryl or aryl substituted with a heteroatom, and/or a C1 to C40 hydrocarbyl, or the reducible Lewis acid represented by the Formula: (Ph$_3$C+), where Ph is phenyl or phenyl substituted with one or more heteroatoms, and/or C1 to C40 hydrocarbyls.

In an embodiment in any of the NCA's comprising an anion represented by Formula 2 described above, the NCA may also comprise a cation represented by the Formula, (L-H)d+, wherein L is an neutral Lewis base; H is hydrogen; (L-H) is a Bronsted acid; and d is 1, 2, or 3, or (L-H)d+ is a Bronsted acid selected from ammoniums, oxoniums, phosphoniums, silyliums, and mixtures thereof.

Further examples of useful activators include those disclosed in U.S. Pat. No. 7,297,653 and U.S. Pat. No. 7,799,879, which are fully incorporated by reference herein.

In an embodiment, an activator useful herein comprises a salt of a cationic oxidizing agent and a noncoordinating, compatible anion represented by the Formula (3):

$$(OX^{e+})_d(A^{d-})_e \quad (3)$$

wherein OX$^{e+}$ is a cationic oxidizing agent having a charge of e+; e is 1, 2, or 3; d is 1, 2, or 3; and A$^{d-}$ is a non-coordinating anion having the charge of d− (as further described above). Examples of cationic oxidizing agents include: ferrocenium, hydrocarbyl-substituted ferrocenium, Ag$^+$, or Pb$^{+2}$. Suitable embodiments of A$^{d-}$ include tetrakis (pentafluorophenyl)-borate.

Activators useful in catalyst systems herein include: trimethylammonium tetrakis(perfluoronaphthyl)borate, N,N-dimethylanilinium tetrakis(perfluoronaphthyl)borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, and the types disclosed in U.S. Pat. No. 7,297,653, which is fully incorporated by reference herein.

Suitable activators also include:
N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis (perfluorophenyl)borate, [Ph3C+][B(C6F5)4-], [Me3NH+][B(C6F5)4-]; 1-(4-(tris(pentafluorophenyl)borate)-2,3,5,6-tetrafluorophenyl)pyrrolidinium; and tetrakis(pentafluorophenyl)orate, 4-(tris(pentafluorophenyl)borate)-2,3,5,6-tetrafluoropyridine.

In an embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate).

In an embodiment, two NCA activators may be used in the polymerization and the molar ratio of the first NCA activator to the second NCA activator can be any ratio. In an embodiment, the molar ratio of the first NCA activator to the second NCA activator is 0.01:1 to 10,000:1, or 0.1:1 to 1000:1, or 1:1 to 100:1.

In an embodiment of the invention, the NCA activator-to-catalyst ratio is a 1:1 molar ratio, or 0.1:1 to 100:1, or 0.5:1 to 200:1, or 1:1 to 500:1 or 1:1 to 1000:1. In an embodiment, the NCA activator-to-catalyst ratio is 0.5:1 to 10:1, or 1:1 to 5:1.

In an embodiment, the catalyst compounds can be combined with combinations of alumoxanes and NCA's (see for example, U.S. Pat. No. 5,153,157, U.S. Pat. No. 5,453,410, EP 0 573 120, WO 94/07928, and WO 95/14044, which discuss the use of an alumoxane in combination with an ionizing activator, all of which are incorporated by reference herein).

In a preferred embodiment of the invention, when an NCA (such as an ionic or neutral stoichiometric activator) is used, the complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately a co-activator or chain transfer agent, such as a group 1, 2, or 13 organometallic species (e.g., an alkyl aluminum compound such as tri-n-octyl aluminum), may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1; 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Chain Transfer Agents

A "chain transfer agent" is any agent capable of hydrocarbyl and/or polymeryl group exchange between a coordinative polymerization catalyst and the metal center of the chain transfer agent during a polymerization process. The chain transfer agent can be any desirable chemical compound such as those disclosed in WO 2007/130306. Preferably, the chain transfer agent is selected from Group 2, 12, or Group 13 alkyl or aryl compounds; preferably zinc, magnesium or aluminum alkyls or aryls; preferably where the alkyl is a C1 to C30 alkyl, alternately a C2 to C20 alkyl, alternately a C3 to 12 alkyl, typically selected independently from methyl, ethyl, propyl, butyl, isobutyl, tertbutyl, pentyl, hexyl, cyclohexyl, phenyl, octyl, nonyl, decyl, undecyl, and dodecyl; and where di-ethylzinc is particularly preferred.

In a particularly useful embodiment, this invention relates to a catalyst system comprising activator, catalyst complex as described herein and chain transfer agent wherein the chain transfer agent is selected from Group 2, 12, or Group 13 alkyl or aryl compounds.

In a particularly useful embodiment, the chain transfer agent is selected from dialkyl zinc compounds, where the alkyl is selected independently from methyl, ethyl, propyl, butyl, isobutyl, tertbutyl, pentyl, hexyl, cyclohexyl, and phenyl.

In a particularly useful embodiment, the chain transfer agent is selected from trialkyl aluminum compounds, where the alkyl is selected independently from methyl, ethyl, propyl, butyl, isobutyl, tertbutyl, pentyl, hexyl, cyclohexyl, and phenyl.

Useful chain transfer agents are typically present at from 10 or 20 or 50 or 100 equivalents to 600 or 700 or 800 or 1000 equivalents relative to the catalyst component. Alternately the chain transfer agent ("CTA") is preset at a catalyst complex-to-CTA molar ratio of from about 1:3000 to 10:1; alternatively 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1.

Useful chain transfer agents include diethylzinc, tri-n-octyl aluminum, trimethylaluminum, triethylaluminum, triisobutylaluminum, tri-n-hexylaluminum, diethyl aluminum chloride, dibutyl zinc, di-n-propylzinc, di-n-hexylzinc, di-n-pentylzinc, di-n-decylzinc, di-n-dodecylzinc, di-n-tetradecylzinc, di-n-hexadecylzinc, di-n-octadecylzinc, diphenylzinc, diisobutylaluminum hydride, diethylaluminum hydride, di-n-octylaluminum hydride, dibutylmagnesium, diethylmagnesium, dihexylmagnesium, and triethylboron.

Supports

In some embodiments, the complexes described herein may be supported (with or without an activator) by any method effective to support other coordination catalyst systems. The catalyst so prepared can be used for oligomerizing or polymerizing olefin in a heterogeneous process. The catalyst precursor, activator, co-activator if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably any support material that has an average particle size greater than 10 μm is suitable for use in this invention. Various embodiments select a porous support material, such as, talc, inorganic oxides, inorganic chlorides, for example, magnesium chloride and resinous support materials, such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component, however, an additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see, for example, the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 m$^2$/g, a pore volume of 0.1-4.0 cc/g and an average particle size of 10-500 μm. Some embodiments select a surface area of 50-500 m$^2$/g, a pore volume of 0.5-3.5 cc/g, or an average particle size of 20-200 μm. Other embodiments select a surface area of 100-400 m$^2$/g, a pore volume of 0.8-3.0 cc/g, and an average particle size of 30-100 μm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

Inventive catalyst complexes are useful in polymerizing unsaturated monomers conventionally known to undergo metallocene-catalyzed polymerization such as solution, slurry, gas-phase, and high-pressure polymerization. Typically one or more of the complexes described herein, one or more activators, and one or more monomers are contacted to produce polymer. In certain embodiments, the complexes may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and, when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in a series reactor operation, in which the above components are added to each of two or more reactors connected in series. The catalyst components can be added to the first reactor in the series. The catalyst component may also be added to both reactors, with one component being added to the first reactor and another component to other reactors. In one preferred embodiment, the complex is activated in the reactor in the presence of olefin.

In a particularly preferred embodiment, the polymerization process is a continuous process.

Polymerization processes used herein typically comprise contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry—in a liquid diluent, or gas phase—in a gaseous diluent). In the case of heterogeneous slurry or gas phase polymerization, the complex and activator may be supported. Silica is useful as a support herein. Chain transfer agents (such as hydrogen, or diethyl zinc) may be used in the practice of this invention.

The present polymerization processes may be conducted under conditions preferably including a temperature of about 30° C. to about 200° C., preferably from about 60° C. to about 195° C., preferably from about 75° C. to about 190° C. The process may be conducted at a pressure of from 0.05 MPa to 1500 MPa. In a preferred embodiment, the pressure is between 1.7 MPa and 30 MPa, or in another embodiment, especially under supercritical conditions, the pressure is between 15 MPa and 1500 MPa.

Monomers

Monomers useful herein include olefins having from 2 to 20 carbon atoms, alternately 2 to 12 carbon atoms (preferably ethylene, propylene, butylene, pentene, hexene, heptene, octene, nonene, decene, and dodecene) and, optionally, also polyenes (such as dienes). Particularly preferred monomers include ethylene, and mixtures of C2 to C10 alpha olefins, such as ethylene-propylene, ethylene-hexene, ethylene-octene, propylene-hexene, and the like.

The complexes described herein are also particularly effective for the polymerization of ethylene, either alone or in combination with at least one other olefinically unsaturated monomer, such as a C3 to C20 α-olefin, and particularly a C3 to C12 α-olefin. Likewise, the present complexes are also particularly effective for the polymerization of propylene, either alone or in combination with at least one other olefinically unsaturated monomer, such as ethylene or a C4 to C20 α-olefin, and particularly a C4 to C20 α-olefin. Examples of preferred α-olefins include ethylene, propylene, butene-1, pentene-1, hexene-1, heptene-1, octene-1, nonene-1, decene-1, dodecene-1, 4-methylpentene-1, 3-methylpentene-1, 3, 5, 5-trimethylhexene-1, and 5-ethylnonene-1.

In some embodiments, the monomer mixture may also comprise one or more dienes at up to 10 wt %, such as from 0.00001 to 1.0 wt %, for example, from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene, 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, and 9-methyl-1,9-decadiene.

Where olefins are used that give rise to short chain branching, such as propylene, the catalyst systems may, under appropriate conditions, generate stereoregular polymers or polymers having stereoregular sequences in the polymer chains.

Scavengers

In some embodiments, when using the complexes described herein, particularly when they are immobilized on a support, the catalyst system will additionally comprise one or more scavenging compounds. Here, the term scavenging compound means a compound that removes polar impurities from the reaction environment. These impurities adversely affect catalyst activity and stability. Typically, the scavenging compound will be an organometallic compound such as the Group-13 organometallic compounds of U.S. Pat. No. 5,153,157; U.S. Pat. No. 5,241,025; WO 91/09882; WO 94/03506; and WO 93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or C6-C20 linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, [$Me_2HNPh$]+[$B(pfp)_4$]- or $B(pfp)_3$ (perfluorophenyl=pfp=$C_6F_5$).

In a preferred embodiment, two or more complexes are combined with diethyl zinc in the same reactor with monomer. Alternately, one or more complexes is combined with another catalyst (such as a metallocene) and a chain transfer agent, such as diethyl zinc and or tri-n-octyl aluminum, in the same reactor with monomer.

Polymer Products

While the molecular weight of the polymers produced herein is influenced by reactor conditions including temperature, monomer concentration and pressure, the presence of chain terminating agents and the like, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC. Preferred polymers produced here may be homopolymers or copolymers. In a preferred embodiment, the comonomer(s) are present at up to 50 mol %, preferably from 0.01 to 40 mol %, preferably 1 to 30 mol %, preferably from 5 to 20 mol %.

In some embodiments herein, a multimodal polyolefin composition is produced, comprising a first polyolefin component and at least another polyolefin component, different from the first polyolefin component by molecular weight, preferably such that the GPC trace has more than one peak or inflection point.

The term "multimodal," when used to describe a polymer or polymer composition, means "multimodal molecular weight distribution," which is understood to mean that the Gel Permeation Chromatography (GPC) trace, plotted as Absorbance versus Retention Time (seconds), has more than one peak or inflection points. An "inflection point" is that point where the second derivative of the curve changes in sign (e.g., from negative to positive or vice versa). For example, a polyolefin composition that includes a first lower molecular weight polymer component (such as a polymer having an Mw of 100,000 g/mol) and a second higher molecular weight polymer component (such as a polymer having an Mw of 300,000 g/mol) is considered to be a "bimodal" polyolefin composition. Preferably the Mw's of the polymer or polymer composition differ by at least 10%, relative to each other, preferably by at least 20%, preferably at least 50%, preferably by at least 100%, preferably by a least 200%. Likewise, in a preferred embodiment, the Mw's of the polymer or polymer composition differ by 10% to 10,000%, relative to each other, preferably by 20% to 1000%, preferably 50% to 500%, preferably by at least 100% to 400%, preferably 200% to 300%.

Unless otherwise indicated, measurements of weight average molecular weight (Mw), number average molecular weight (Mn), and z average molecular weight (Mz) are determined by Gel Permeation Chromatography (GPC) as described in Macromolecules, 2001, Vol. 34, No. 19, pg. 6812, which is fully incorporated herein by reference, including that, a High Temperature Size Exclusion Chromatograph (SEC, Waters Alliance 2000), equipped with a differential refractive index detector (DRI) equipped with three Polymer Laboratories PLgel 10 mm Mixed-B columns is used. The instrument is operated with a flow rate of 1.0 cm3/min, and an injection volume of 300 µL. The various transfer lines, columns and differential refractometer (the DRI detector) are housed in an oven maintained at 145° C.

Polymer solutions are prepared by heating 0.75 to 1.5 mg/mL of polymer in filtered 1,2,4-Trichlorobenzene (TCB) containing ~1000 ppm of butylated hydroxy toluene (BHT) at 160° C. for 2 hours with continuous agitation. A sample of the polymer containing solution is injected into to the GPC and eluted using filtered 1,2,4-trichlorobenzene (TCB) containing ~1000 ppm of BHT. The separation efficiency of the column set is calibrated using a series of narrow MWD polystyrene standards reflecting the expected Mw range of the sample being analyzed and the exclusion limits of the column set. Seventeen individual polystyrene standards, obtained from Polymer Laboratories (Amherst, Mass.) and ranging from Peak Molecular Weight (Mp) ~580 to 10,000, 000, were used to generate the calibration curve.

The flow rate is calibrated for each run to give a common peak position for a flow rate marker (taken to be the positive inject peak) before determining the retention volume for each polystyrene standard. The flow marker peak position is used to correct the flow rate when analyzing samples. A calibration curve (log(Mp) vs. retention volume) is generated by recording the retention volume at the peak in the DRI signal for each PS standard, and fitting this data set to a 2nd-order polynomial. The equivalent polyethylene molecular weights are determined by using the Mark-Houwink coefficients shown in the Table below.

| Mark-Houwink coefficients | | |
| --- | --- | --- |
| Material | K (dL/g) | α |
| PS | $1.75 \times 10^{-4}$ | 0.67 |
| PE | $5.79 \times 10^{-4}$ | 0.695 |

In the Experimental section below, molecular weight data from a different method called a "Rapid GPC" is reported. In the event of a conflict between the above method and the Rapid GPC method, the above method shall be used.

In a preferred embodiment, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC and have a multi-modal, preferably bimodal, Mw/Mn.

In a preferred embodiment of the invention, an ethylene polymer is produced, particularly a polymer of ethylene, either alone or in combination with at least one other olefinically unsaturated monomer, such as a C3 to C20 α-olefin, and particularly a C3 to C12 α-olefin. In a preferred embodiment of the invention, a propylene polymer is produced, either alone or in combination with at least one other olefinically unsaturated monomer, such as ethylene or a C4 to C20 α-olefin, and particularly a C4 to C20 α-olefin. Examples of preferred α-olefins include ethylene, propylene, butene-1, pentene-1, hexene-1, heptene-1, octene-1, nonene-1, decene-1, dodecene-1, 4-methylpentene-1, 3-methylpentene-1, 3, 5, 5-trimethylhexene-1, and 5-ethylnonene-1.

In a preferred embodiment of the invention, the polymers produced herein are homopolymers of ethylene or copolymers of ethylene preferably having from 0 to 25 mol % (alternately from 0.5 to 20 mol %, alternately from 1 to 15 mol %, preferably from 3 to 10 mol %) of one or more C3 to C20 olefin comonomer (preferably C3 to C12 alpha-olefin, preferably propylene, butene, hexene, octene, decene, dodecene, preferably propylene, butene, hexene, octene).

In a preferred embodiment of the invention, the polymers produced herein are homopolymers of propylene or are copolymers of propylene preferably having from 0 to 25 mol % (alternately from 0.5 to 20 mol %, alternately from 1 to 15 mol %, preferably from 3 to 10 mol %) of one or more of C2 or C4 to C20 olefin comonomer (preferably ethylene or C4 to C12 alpha-olefin, preferably ethylene, butene, hexene, octene, decene, dodecene, preferably ethylene, butene, hexene, octene). In a preferred embodiment of the invention, the monomer is ethylene and the comonomer is hexene, preferably from 0.5 to 15 mol % hexene, alternately 1 to 10 mol %.

In some embodiments, the polymer (such as an ethylene copolymer or a propylene copolymer) may also comprise one or more dienes at up to 10 wt %, such as from 0.00001 to 1.0 wt %, for example from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene, 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1 and 9-methyl-1,9-decadiene.

End Uses

Articles made using polymers produced herein may include, for example, molded articles (such as containers and bottles, e.g., household containers, industrial chemical containers, personal care bottles, medical containers, fuel tanks, and storageware, toys, sheets, pipes, tubing) films, non-wovens, and the like. It should be appreciated that the list of applications above is merely exemplary, and is not intended to be limiting.

In another embodiment, this invention relates to:

1. A pyridylamide transition metal complex (optionally for use in alkene polymerization) represented by the Formula (I), (II), or (III):

wherein:

M is a Group 3, 4, or 5 metal;

Q is -(TT)- or -(TTT)-, where each T is a substituted or unsubstituted group 14, 15, or 16 element so that together with the "—C—N═C—" fragment it forms a 5- or 6-membered heterocycle;

$R^1$ is selected from hydrocarbyls, substituted hydrocarbyls, and polar groups;

each $R^2$ and $R^3$ is independently selected from hydrogen, halogen, hydrocarbyls, substituted hydrocarbyls, and polar groups, and $R^2$ and $R^3$ may be joined to form a ring;

each $R^4$, $R^5$, $R^6$, $R^7$, $R^8$, $R^9$, $R^{10}$, $R^{11}$, $R^{12}$, $R^{13}$, and $R^{14}$ is independently selected from hydrogen, halogen, hydrocarbyls, substituted hydrocarbyls, and polar groups, and any adjacent R groups may join to form a carbocyclic or heterocyclic ring, which may be substituted or unsubstituted;

$R^3$ and $R^4$ may be joined to form a ring (preferably a 5-membered ring with the joined $R^3R^4$ group being —$CH_2CH_2$—, or a 6-membered ring with the joined $R^{10}R^{11}$ group being —$CH_2CH_2CH_2$—);

J is an aromatic group containing 4 to 40 carbon atoms that coordinates to the metal center through a carbanion donor;

each X is an anionic leaving group, where the X groups may be the same or different and any two X groups may be linked to form a dianionic leaving group;

each L is a neutral Lewis base and any two L groups may be joined to form a bidentate Lewis base;

X and L groups may be covalently joined;

n is 1, 2, or 3;

y is 0, 1, or 2;

wherein n+y is no greater than 4.

2. The complex of paragraph 1, wherein M is Ti, Zr, or Hf.

3. The complex of paragraph 1 or 2, wherein R² is hydrogen, alkyl, aryl, or halogen; and R³ is hydrogen, alkyl, aryl, or halogen.

4. The complex of paragraph 1, 2, or 3, wherein R¹ is selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

5. The complex of any of paragraphs 1 to 4, wherein each L is independently selected from the group consisting of ethers, thio-ethers, amines, nitriles, imines, pyridines, and phosphines.

6. The complex of any of paragraphs 1 to 5, wherein each X is independently selected from the group consisting of halide, alkyl, aryl, alkoxy, amido, hydrido, phenoxy, hydroxy, alkylsulfonate, carboxylate, silyl, allyl, alkenyl, and alkynyl.

7. The complex of paragraph 1, wherein, R¹ is one or more of 2-methylphenyl, 2-isopropylphenyl, 2-ethylphenyl, 2,6-dimethylphenyl, mesityl, 2,6-diethylphenyl, 2,6-diisopropylphenyl, and 2,4,6-triisopropylphenyl.

8. The complex of paragraph 1, wherein, M is Zr or Hf, R² and R³ are both hydrogen, and J is an aromatic carbocycle containing between 6 and 14 carbons.

9. The complex of paragraph 1, wherein, M is a group 4 metal, R² is hydrogen, R³ and R⁴ are joined to form a 5-membered ring, with the R³R⁴ unit being —CH₂CH₂—.

10. The complex of paragraph 1, wherein, M is a group 4 metal, R² is hydrogen, R³ and R⁴ are joined to form a 6-membered ring, with the R³R⁴ unit being —CH₂CH₂CH₂—.

11. A catalyst system comprising an activator and the transition metal complex of any of paragraphs 1 to 10.

12. The catalyst system of paragraph 11, wherein the activator comprises a non-coordinating anion and/or an alumoxane.

13. The catalyst system of paragraph 11 or 12, wherein the catalyst system is supported.

14. The catalyst system of paragraph 11, 12, or 13, wherein the complex is represented by the Formula (A) or (B):

(A)

(B)

15. The system of any of paragraphs 11 to 14, wherein the transition metal complex is supported.

16. A polymerization process to produce polyolefin comprising contacting one or more olefin monomers with the catalyst system of any of paragraphs 11 to 15 and obtaining olefin polymer.

17. The process of paragraph 16, wherein the monomer comprises ethylene and/or propylene.

EXPERIMENTAL

¹H NMR spectroscopic data were acquired at 400 MHz using solutions prepared by dissolving approximately 10 mg (approx. 0.2M) of a sample in C6D6. The chemical shifts (δ) presented are relative to the residual protium in the deuterated solvent at 7.15 ppm.

Examples

Specific examples of ligands that have been prepared are shown below:

(1)

(2)

Specific examples of pre-catalyst complexes that have been prepared are shown below:

(A)

(B)

The synthetic route used to prepare complex B is described below. Complex A was synthesized in an analogous fashion using 2-bromo-6-naphthylpyridine in place of 2-bromo-6-phenylpyridine.

Synthesis of 2-bromo-6-phenylpyridine. Butyllithium (50 mL, 118 mmol), hexanes (100 mL) and dimethylaminoethanol (5.91 mL, 59.0 mmol) were combined and cooled to −10° C., 2-Phenylpyridine (7.63 g, 49.2 mmol) was added dropwise over 5 minutes to form a clear orange solution. After 1 h, the solution had darkened to red-orange. The solution was then cooled to −40° C. and THF (500 mL) that had been cooled to −35° C. was added. Immediately 1,2-dibromoethane (25.4 mL, 295 mmol) was added in one portion, and the mixture was warmed to ambient temperature. The volatiles were removed by evaporation and the yellow oily paste was dissolved in Et$_2$O (125 mL) and water (100 mL). The aqueous layer was removed and the organics were dried over brine, then sodium sulfate. Evaporation of the ether afforded crude product that was crystallized from hexanes as yellow crystals (8.0 g, 69%).

Synthesis of 2,6-diisopropyl-N-((1-(6-phenylpyridin-2-yl)naphthalen-2-yl)methyl)aniline (1). Sodium carbonate (0.567 g, 5.35 mmol) was dissolved in MeOH (20 ml) and water (80 ml) and sparged with N$_2$ for 30 min. The obtained solution was added to a mixture of 2-bromo-6-phenylpyridine (0.476 g, 2.03 mmol), 2,6-diisopropyl-N-((1-(4,4,5,5-tetramethyl-1,3,2-dioxaborolan-2-yl)naphthalen-2-yl)methyl)aniline (0.904 g, 2.04 mmol) and Pd(PPh$_3$)$_4$ (0.124 g, 0.107 mmol) dissolved in toluene (75 ml) under N$_2$ atmosphere. The mixture was heated to reflux for 12 h and then cooled to room temperature. The organic layer was separated, dried over brine, then sodium sulfate and the solvent removed. The product was isolated by column chromatography on silica gel using hexanes-EtOAc (20:1, v/v) as eluent. The product was obtained as a white solid (0.630 mg, 66%).

Synthesis of 2,6-diisopropyl-N-(2-(6-phenylpyridin-2-yl)benzyl)aniline (2). Sodium carbonate (0.445 g, 4.20 mmol) was dissolved in MeOH (25 ml) and water (75 ml) and sparged with N$_2$ for 30 min. The obtained solution was added to a mixture of 2-bromo-6-phenylpyridine (0.392 g, 1.67 mmol), 2,6-diisopropyl-N-(2-(4,4,5,5-tetramethyl-1,3,2-dioxaborolan-2-yl)benzyl)aniline (0.660 g, 1.67 mmol) and Pd(PPh$_3$)$_4$ (0.115 g, 0.099 mmol) dissolved in toluene (60 ml) under a nitrogen atmosphere. The mixture was heated to reflux for 12 h and then cooled to room temperature. The organic layer was separated, dried over brine, then magnesium sulfate and the solvent removed. The product was isolated by column chromatography on silica gel using hexanes-EtOAc (50:1, v/v) as eluent offering the product (0.619 mg, 88%).

Synthesis of complex A. Toluene (10 mL) was added to ligand 1 (0.207 g, 0.440 mmol) and tetrabenzylhafnium (0.263 g, 0.484 mmol). The mixture was heated to 100° C. while shielded from light. After 15 hours the volatiles were evaporated to afford a residue that was washed thoroughly with pentane to give a yellow-orange solid of complex A (0.30 g, 81%).

Synthesis of complex B. A mixture of dodecane (5 mL) and toluene (1 mL) was added to ligand 2 (0.228 g, 0.542 mmol) and tetrakis(dimethylamido)hafnium (0.192 g, 0.542 mmol). The mixture was heated to 150° C. After 16 hours the volatiles were evaporated to afford the bis(amide) complex [(ligand (2))Hf(NMe$_2$)$_2$] as a yellow-orange solid (0.355 g, 95.6%). A portion of the bis(amide) complex (0.274 g, 0.400 mmol) was combined with toluene (8 mL) to form a yellow suspension. Trimethylaluminum (0.288 g, 4.00 mmol) was then added dropwise over a minute. The mixture was heated to 50° C. for 30 minutes and then the volatiles were evaporated under a stream of nitrogen. The product was washed with pentane and dried under reduced pressure (0.14 g, 56%).

Polymerization Examples.

Olefin polymerizations were carried out in a high throughput parallel, pressure reactor, as generally described in U.S. Pat. No. 6,306,658; U.S. Pat. No. 6,455,316; U.S. Pat. No. 6,489,168; WO 00/09255; and Murphy et al., J. Am. Chem. Soc., 2003, Vol. 125, pp. 4306-4317, each of which is fully incorporated herein by reference to the extent not inconsistent with this specification. The following describes a general procedure used to screen catalysts. The desired temperatures, pressures, quantities of chemicals used (e.g., pre-catalysts, activators, scavengers, chain transfer agents, etc.) will vary from experiment to experiment, and specific values are given in the Tables below where data are presented.

A pre-weighed glass vial insert and disposable stirring paddle were fitted to each reaction vessel of the reactor, which contains 48 individual reaction vessels. The reactor was then closed and each vessel was individually heated to the desired temperature and pressurized to a predetermined pressure (typically 75 psi=0.517 MPa). If desired, 1-octene was then injected into each reaction vessel through a valve, followed by enough solvent (typically isohexane or toluene) to bring the total reaction volume, including the subsequent additions, to the desired volume (typically 5 mL). The contents of the vessel were then stirred at 800 rpm. A solution of scavenger (typically an organoaluminum reagent in isohexane or toluene) was then added along with a solvent chaser (typically 500 microliters). If desired, a solution of an additional scavenger or chain transfer agent was then added along with a solvent chaser (typically 500 microliters). An activator solution in toluene (typically 1 molar equivalent relative to the pre-catalyst complex) was then injected into the reaction vessel along with a solvent chaser (typically 500 microliters). Then a toluene solution of the pre-catalyst complex dissolved was added along with a solvent chaser (typically 500 microliters).

The reaction was then allowed to proceed until either a set amount of ethylene pressure had been taken up by the polymerization (typically 12 psi=0.137 MPa for reactions performed at 75 psi) or a specific amount of time had passed (typically 10 to 20 minutes). At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight.

To determine various molecular weight related values by GPC, high temperature size exclusion chromatography was performed using an automated "Rapid GPC" system. This apparatus has a series of three 30 cm×7.5 mm linear columns, each containing PLgel 10 um, Mix B. The GPC system was calibrated using polystyrene standards ranging from 580 g/mol-3,390,000 g/mol. The system was operated at an eluent flow rate of 2.0 mL/min and an oven temperature of 165° C. 1,2,4-trichlorobenzene was used as the eluent. The polymer samples were dissolved in 1,2,4-trichlorobenzene at a concentration of 0.1-0.9 mg/mL. 250 μL of a polymer solution was injected into the system. The concentration of the polymer in the eluent was monitored using an evaporative light scattering detector. The molecular weights presented in the examples are relative to linear polystyrene standards.

Differential Scanning calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period.

Data shown in Table 1 indicates that activated complexes of the general type described in this invention are capable of polymerizing alkenes. Table 1 shows polymerization results and polymer characterization data for ethylene-octene copolymerization performed with activated complexes A and B. Conditions for runs 1 to 6 were as follows: polymerization temperature 80° C., isohexane solvent, total volume=5 mL, 75 psi ethylene, amount of Complex A or B=20 nmol, activator was N,N-dimethylanilinium tetrakis(pentafluorophenyl)borate, and the activator/complex ratio was 1:1.

TABLE 1

| run | complex | time (sec) | yield (mg) | activity (g/mmol/h/bar) | Mw (g/mol) | Mn (g/mol) | Tm (° C.) |
|---|---|---|---|---|---|---|---|
| 1 | A | 64 | 34 | 18,377 | 134,292 | 88,893 | 101.9 |
| 2 | A | 49 | 32 | 22,395 | 125,919 | 81,902 | 103.3 |
| 3 | A | 63 | 31 | 17,147 | 123,060 | 82,808 | 103.6 |
| 4 | B | 73 | 33 | 15,866 | 135,753 | 89,844 | 100.2 |
| 5 | B | 48 | 26 | 18,811 | 111,772 | 70,320 | 100.5 |
| 6 | B | 59 | 26 | 15,587 | 114,220 | 69,979 | 102.0 |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element, or a group of elements is preceded with the transitional phrase "comprising", it is understood that we also contemplate the same composition or group of elements with transitional phrases "consisting essentially of," "consisting of", "selected from the group consisting of," or "is" preceding the recitation of the composition, element, or elements and vice versa.

What is claimed is:

1. A transition metal complex represented by the Formula (I):

wherein:

M is a Group 3, 4, or 5 metal;

Q is -(TT)- or -(TTT)-, where each T is a substituted or unsubstituted group 14, 15, or 16 element so that, together with the "—C—N═C—" fragment, it forms a 5- or 6-membered heterocycle;

$R^1$ is selected from hydrocarbyls, substituted hydrocarbyls, or polar groups;

each $R^2$ and $R^3$ is independently selected from hydrogen, halogen, hydrocarbyls, substituted hydrocarbyls, or polar groups, and $R^2$ and $R^3$ may be joined to form a ring;

each $R^4$, $R^5$, $R^6$, and $R^7$ is independently selected from hydrogen, halogen, hydrocarbyls, substituted hydrocarbyls, and polar groups, and any adjacent R groups may join to form a carbocyclic or heterocyclic ring, which may be substituted or unsubstituted;

$R^3$ and $R^4$ may be joined to form a ring;

J is an aromatic group containing 4 to 40 carbon atoms that coordinates to the metal center through a carbanion donor;

each X is an anionic leaving group, where the X groups may be the same or different and any two X groups may be linked to form a dianionic leaving group;

each L is a neutral Lewis base and any two L groups may be joined to form a bidentate Lewis base;

X and L groups may be covalently joined;

n is 1, 2, or 3;

y is 0, 1, or 2;

wherein n+y is no greater than 4.

2. The complex of claim 1, wherein the complex is represented by Formula II:

(II)

wherein:

M is a Group 3, 4, or 5 metal;

$R^1$ is selected from hydrocarbyls, substituted hydrocarbyls, or polar groups;

each $R^2$ and $R^3$ is independently selected from hydrogen, halogen, hydrocarbyls, substituted hydrocarbyls, or polar groups, and $R^2$ and $R^3$ may be joined to form a ring;

each $R^4$, $R^5$, $R^6$, $R^7$, $R^8$, $R^9$, and $R^{10}$ is independently selected from hydrogen, halogen, hydrocarbyls, substituted hydrocarbyls, or polar groups, and any adjacent R groups may join to form a carbocyclic or heterocyclic ring, which may be substituted or unsubstituted;

$R^3$ and $R^4$ may be joined to form a ring;

J is an aromatic group containing 4 to 40 carbon atoms that coordinates to the metal center through a carbanion donor;

each X is an anionic leaving group, where the X groups may be the same or different and any two X groups may be linked to form a dianionic leaving group;

each L is a neutral Lewis base and any two L groups may be joined to form a bidentate Lewis base;

X and L groups may be covalently joined;

n is 1, 2, or 3;

y is 0, 1, or 2;

wherein n+y is no greater than 4.

3. The complex of claim 1, wherein the complex is represented by Formula III:

(III)

wherein:

M is a Group 3, 4, or 5 metal;

$R^1$ is selected from hydrocarbyls, substituted hydrocarbyls, or polar groups;

each $R^2$ and $R^3$ is independently selected from hydrogen, halogen, hydrocarbyls, substituted hydrocarbyls, or polar groups, and $R^2$ and $R^3$ may be joined to form a ring;

each $R^4$, $R^5$, $R^6$, $R^7$, $R^8$, $R^9$, $R^{10}$, $R^{11}$, $R^{12}$, $R^{13}$, and $R^{14}$ is independently selected from hydrogen, halogen, hydrocarbyls, substituted hydrocarbyls, or polar groups, and any adjacent R groups may join to form a carbocyclic or heterocyclic ring, which may be substituted or unsubstituted;

$R^3$ and $R^4$ may be joined to form a ring and $R^{10}$ and $R^{11}$ may be joined to form a ring;

each X is an anionic leaving group, where the X groups may be the same or different and any two X groups may be linked to form a dianionic leaving group;

each L is a neutral Lewis base and any two L groups may be joined to form a bidentate Lewis base;

X and L groups may be covalently joined;

n is 1, 2, or 3;

y is 0, 1, or 2;

wherein n+y is no greater than 4.

4. The complex of claim 1, wherein M is Ti, Zr, or Hf.

5. The complex of claim 1, wherein $R^2$ is hydrogen, alkyl, aryl, or halogen; and $R^3$ is hydrogen, alkyl, aryl, or halogen.

6. The complex of claim 3, wherein $R^1$ contains from 1 to 30 carbon atoms.

7. The complex of claim 1, wherein $R^1$ is selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups having from one to ten carbons.

8. The complex of claim 1, wherein each L is independently selected from the group consisting of ethers, thioethers, amines, nitriles, imines, pyridines, and phosphines.

9. The complex of claim 1, wherein each X is independently selected from the group consisting of halide, alkyl, aryl, alkoxy, amido, hydrido, phenoxy, hydroxy, alkylsulfonate, carboxylate, silyl, allyl, alkenyl, and alkynyl.

10. The complex of claim 1, wherein, $R^1$ is one or more of 2-methylphenyl, 2-isopropylphenyl, 2-ethylphenyl, 2,6-dimethylphenyl, mesityl, 2,6-diethylphenyl, 2,6-diisopropylphenyl, and 2,4,6-triisopropylphenyl.

11. The complex of claim 1, wherein, M is Sc, Y, Ti, Zr, Hf, V, Nb, or Ta.

12. The complex of claim 1, wherein, M is Zr or Hf, $R^2$ and $R^3$ are both hydrogen, and J is an aromatic carbocycle containing between 6 and 14 carbons.

13. The complex of claim 1, wherein, M is a group 4 metal, $R^2$ is hydrogen, $R^3$ and $R^4$ are joined to form a 5-membered ring, with the $R^3R^4$ unit being —$CH_2CH_2$—.

14. The complex of claim 1, wherein, M is a group 4 metal, $R^2$ is hydrogen, $R^3$ and $R^4$ are joined to form a 6-membered ring, with the $R^3R^4$ unit being —$CH_2CH_2CH_2$—.

15. A catalyst system comprising an activator and the transition metal complex of claim 1.

16. The catalyst system of claim 15, wherein the activator comprises a non-coordinating anion.

17. The catalyst system of claim 15, wherein the activator comprises an alumoxane.

18. The catalyst system of claim 15, wherein the catalyst system is supported.

19. The catalyst system of claim 15, wherein the complex is represented by the Formula (A) or (B):

(A)

(B)

20. A polymerization process to produce polyolefin comprising contacting one or more olefin monomers with the catalyst system of claim 15 and obtaining olefin polymer.

21. The process of claim 20, wherein the activator comprises an alumoxane.

22. The process of claim 20, wherein the activator comprises a non-coordinating anion.

23. The process of claim 20, wherein the monomer comprises ethylene and/or propylene.

24. The process of claim 20, wherein the transition metal complex is supported.

25. A complex represented by the Formula:

wherein:

M is a Group 3, 4, or 5 metal;

Q is -(TT)- or -(TTT)-, where each T is a substituted or unsubstituted group 14, 15, or 16 element so that together with the "—C—N═C—" fragment, it forms a 5- or 6-membered heterocycle;

$R^1$ is selected from hydrocarbyls, substituted hydrocarbyls, or polar groups;

each $R^2$ and $R^3$ is independently selected from hydrogen, halogen, hydrocarbyls, substituted hydrocarbyls, or polar groups, and $R^2$ and $R^3$ may be joined to form a ring;

each $R^4$, $R^5$, $R^6$, and $R^7$ is independently selected from hydrogen, halogen, hydrocarbyls, substituted hydrocarbyls, or polar groups, and any adjacent R groups may join to form a carbocyclic or heterocyclic ring, which may be substituted or unsubstituted;

$R^3$ and $R^4$ may be joined to form a ring or $R^{10}$ and $R^{11}$ may be joined to form a ring;

HJ is a non-coordinated aromatic group containing 4 to 40 carbon atoms that can be deprotonated to form a group that coordinates to the metal center through a carbanion donor;

each X is an anionic leaving group, where the X groups may be the same or different and any two X groups may be linked to form a dianionic leaving group;

each L is a neutral Lewis base and any two L groups may be joined to form a bidentate Lewis base;

X and L groups may be covalently joined;

n is 1, 2, or 3;

y is 0, 1, or 2;

wherein n+y is no greater than 4.

\* \* \* \* \*

UNITED STATES PATENT AND TRADEMARK OFFICE
CERTIFICATE OF CORRECTION

PATENT NO. : 9,598,444 B2 Page 1 of 1
APPLICATION NO. : 15/153247
DATED : March 21, 2017
INVENTOR(S) : John R. Hagadorn and Patrick J. Palafox It is certified that error appears in the above-identified patent and that said Letters Patent is hereby corrected as shown below:

In Claim 1, Column 30, Line 48, please remove "and" before "polar groups" and replace it with --or--.

Signed and Sealed this
Third Day of October, 2017

Joseph Matal
*Performing the Functions and Duties of the*
*Under Secretary of Commerce for Intellectual Property and*
*Director of the United States Patent and Trademark Office*